(12) United States Patent
Handa et al.

(10) Patent No.: US 11,220,516 B2
(45) Date of Patent: Jan. 11, 2022

(54) NITRIC OXIDE-RELEASING ANTIBIOTICS, METHODS OF MAKING, AND METHODS OF USE

(71) Applicant: University of Georgia Research Foundation, Inc., Athens, GA (US)

(72) Inventors: Hitesh Handa, Athens, GA (US); Sean P. Hopkins, Athens, GA (US); Priyadarshini Singha, Lake Forest, CA (US); Christina Danielle Workman, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/005,373

(22) Filed: Aug. 28, 2020

(65) Prior Publication Data

US 2021/0061817 A1 Mar. 4, 2021

Related U.S. Application Data

(60) Provisional application No. 62/893,897, filed on Aug. 30, 2019.

(51) Int. Cl.
*A01N 51/00* (2006.01)
*C07D 499/897* (2006.01)
*C07D 499/12* (2006.01)

(52) U.S. Cl.
CPC ......... *C07D 499/897* (2013.01); *A01N 51/00* (2013.01); *C07D 499/12* (2013.01)

(58) Field of Classification Search
CPC .................................................... A01N 51/00
See application file for complete search history.

(56) References Cited

U.S. PATENT DOCUMENTS

| 2013/0026156 | A1 | 1/2013 | Naylor et al. |
| 2015/0023866 | A1 | 1/2015 | Montgomery et al. |
| 2015/0297547 | A1* | 10/2015 | Peng ............... A61K 31/496 514/23 |
| 2017/0002810 | A1 | 1/2017 | Kim et al. |

FOREIGN PATENT DOCUMENTS

| WO | 20181112405 | 6/2018 |
| WO | 2019079765 | 4/2019 |

OTHER PUBLICATIONS

Friedman et al (Nitric Oxide 25 (2011) 381-386) (Year: 2011).*
Donlan, R. M., Biofilms: Microbial Life on Surfaces. Emerg. Infect. Dis. 2002, 8 (9), 881.

(Continued)

*Primary Examiner* — Benjamin J Packard
(74) *Attorney, Agent, or Firm* — Thomas | Horstemeyer, LLP

(57) ABSTRACT

The present disclosure provides for modified antibiotic compounds, methods of making modified antibiotic compounds, methods of use, products including modified antibiotic compounds, and the like. The modified antibiotic compound comprises a nitric oxide release agent covalently attached to an antibiotic molecule, such as S-nitroso-N-acetylpenicillamine covalently attached to ampicillin.

20 Claims, 9 Drawing Sheets

(56) References Cited

OTHER PUBLICATIONS

Bjarnsholt, T.; Jensen, P. O.; Fiandaca, M. J.; Pedersen, J.; Hansen, C. R.; Andersen, C. B.; Pressler, T.; Givskov, M. Hiby, N., Pseudomonas Aeruginosa Biofilms in the Respiratory Tract of Cystic Fibrosis Patients. Pediatr. Pulmonol. 2009, 44 (6), 547-558.
Deri, H.; Olson, M.; Stremick, C.; Read, R.; Morck, D.; Buret, A., The Calgary Biofilm Device: New Technology for Rapid Determination of Antibiotic Susceptibilities of Bacterial Biofilms. J. Clin. Microbiol. 1999, 37 (6), 1771-1776.
Furchgott, R. F., Role of Endothelium in Responses of Vascular Smooth Muscle. Circ. Res. 1983, 53 (5), 557-573.
Radomski, M.; Palmer, R.; Moncada, S., Endogenous Nitric Oxide Inhibits Human Platelet Adhesion to Vascular Endothelium. The Lancet 1987, 330 (8567), 1057-1058.
Macmicking, J.; Xie, Q.-w.; Nathan, C., Nitric Oxide and Macrophage Function. Annu. Rev. Immunol. 1997,15 (1), 323-350.
Keefer, L. K.; Saavedra, J. E., Nitrogen-Based Diazeniumdiolates: Versatile Nitric Oxide-Releasing Compounds for Biomedical Research and Potential Clinical Applications. J. Chem. Educ. 2002, 79 (12), 1427.
Haitham, A.-S. D.; Ferro, A., S-Nitrosothiols: A Class of Nitric Oxide-Donor Drugs. Clin. Sci. 2000, 98 (5), 507-520.
Pant, J.; Goudie, M. J.; Hopkins, S. P.; Brisbois, E. J.; Handa, H., Tunable Nitric Oxide Release from S-Nitroso-N-Acetylpenicillamine Via Catalytic Copper Nanoparticles for Biomedical Applications. ACS Appl. Mater. Interfaces 2017, 9(18), 15254-15264.
Lu, Y.; Slomberg, D. L.; Shah, A.; Schoenfisch, M. H., Nitric Oxide-Releasing Amphiphilic Poly(Amidoamine)(Pamam) Dendrimers as Antibacterial Agents. Biomacromolecules 2013,14 (10), 3589-3598.
Hopkins, S. P.; Pant, J.; Goudie, M. J.; Schmiedt, C.; Handa, H., Achieving Long-Term Biocompatible Silicone Via Covalently Immobilized S-Nitroso-N-Acetylpenicillamine (Snap) That Exhibits 4 Months of Sustained Nitric Oxide Release. ACS Appl. Mater. Interfaces 2018, 10 (32), 27316-27325.
Hetrick, E. M.; Schoenfisch, M. H., Antibacterial Nitric Oxide-Releasing Xerogels: Cell Viability and Parallel Plate Flow Cell Adhesion Studies. Biomaterials 2007, 28 (11), 1948-1956.
Barraud, N.; J Kelso, M.; A Rice, S.; Kjelleberg, S., Nitric Oxide: A Key Mediator of Biofilm Dispersal with Applications n Infectious Diseases. Curr. Pharm. Des. 2015,21 (1), 31-42.
Schairer, D. O.; Chouake, J. S.; Nosanchuk, J. D.; Friedman, A. J., The Potential of Nitric Oxide Releasing Therapies as Antimicrobial Agents. Virulence 2012, 3 (3), 271-279.
Ren, H.; Wu, J.; Colletta, A.; Meyerhoff, M. E.; Xi, C., Efficient Eradication of Mature Pseudomonas Aeruginosa Biofilm Via Controlled Delivery of Nitric Oxide Combined with Antimicrobial Peptide and Antibiotics. Front. Microbiol. 2016, 7, 1260.
Reffuveille, F.; Fairfull-Smith, K. E.; Hancock, R. E., Potentiation of Ciprofloxacin Action against Gram-Negative Bacterial Biofilms by a Nitroxide. Pathogens and disease 2015, 73 (5).
Craven, M.; Kasper, S.; Canfield, M.; Diaz-Morales, R.; Hrabie, J.; Cady, N.; Strickland, A., Nitric Oxide-Releasing Polyacrylonitrile Disperses Biofilms Formed by Wound-Relevant Pathogenic Bacteria. J. Appl. Microbiol. 2016,120 (4), 1085-1099.
Duong, H. T.; Jung, K.; Kutty, S. K.; Agustina, S.; Adnan, N. N. M.; Basuki, J. S.; Kumar, N.; Davis, T. P.; Barraud, N. Boyer, C., Nanoparticle (Star Polymer) Delivery of Nitric Oxide Effectively Negates Pseudomonas Aeruginosa Biofilm Formation. Biomacromolecules 2014,15 (7), 2583-2589.
Namivandi-Zangeneh, R.; Sadrearhami, Z.; Bagheri, A.; Sauvage-Nguyen, M.; Ho, K. K. K.; Kumar, N.; Wong, E. H. Boyer, C., Nitric Oxide-Loaded Antimicrobial Polymer for the Synergistic Eradication of Bacterial Biofilm. ACS Macro Letters 2018, 7 (5), 592-597.
Barraud, D.; Schleheck, D.; Klebensberger, J.; Webb, J. S.; Hassett, D. J.; Rice, S. A.; Kjelleberg, S., Nitric Oxide Signaling in Pseudomonas Aeruginosa Biofilms Mediates Phosphodiesterase Activity, Decreased Cyclic Di-Gmp Levels, and Enhanced Dispersal. J. Bacteriol. 2009, 191 (23), 7333-7342.
Howlin, R. P.; Cathie, K.; Hall-Stoodley, L.; Cornelius, V.; Duignan, C.; Allan, R. N.; Fernandez, B. 0.; Barraud, N. Bruce, K. D.; Jefferies, J., Low-Dose Nitric Oxide as Targeted Anti-Biofilm Adjunctive Therapy to Treat Chronic Pseudomonas Aeruginosa Infection in Cystic Fibrosis. Mol. Ther. 2017,25 (9), 2104-2116.
Moynihan, H. A.; Roberts, S. M., Preparation of Some Novel S-Nitroso Compounds as Potential Slow-Release Agents of Nitric Oxide in Vivo. J. Chem. Soc., Perkin Trans. 1 1994, (7), 797-805.
Ellman, G. L., Tissue Sulfhydryl Groups. Arch. Biochem. Biophys. 1959, 82 (1), 70-77.
Khan, A. A. P.; Mohd, A.; Bano, S.; Siddiqi, K.; Asiri, A. M., Spectrophotometric Methods for the Determination of Ampicillin by Potassium Permanganate and 1-Chloro-2,4-Dinitrobenzene in Pharmaceutical Preparations. Arabian Journal of Chemistry 2015, 8 (2), 255-263.
Worley, B. V.; Slomberg, D. L.; Schoenfisch, M. H., Nitric Oxide-Releasing Quaternary Ammonium-Modified Poly Amidoamine) Dendrimers as Dual Action Antibacterial Agents. Bioconjug. Chem. 2014, 25 (5), 918-927.
Privett, B. J.; Deupree, S. M.; Backlund, C. J.; Rao, K. S.; Johnson, C. B.; Coneski, P. N.; Schoenfisch, M. H., Synergy of Nitric Oxide and Silver Sulfadiazine against Gram-Negative, Gram-Positive, and Antibiotic-Resistant Pathogens. Mol. Pharm. 2010, 7 (6), 2289-2296.
Verderosa, A. D.; Mansour, S. C.; de la Fuente-Núñez, C.; Hancock, R. E.; Fairfull-Smith, K. E., Synthesis and Evaluation of Ciprofloxacin-Nitroxide Conjugates as Anti-Biofilm Agents. Molecules 2016,21 (7), 841.
Logghe, C.; Van Ossel, C.; D'Hoore, W.; Ezzedine, H.; Wauters, G.; Haxhe, J.-J., Evaluation of Chlorhexidine and Silver-Sulfadiazine Impregnated Central Venous Catheters for the Prevention of Bloodstream Infection in Leukaemic Patients: A Randomized Conlrolled Trial. J. Hosp. Infect. 1997, 37 (2), 145-156.
León, C.; Ruiz-Santana, S.; Rello, J.; Maria, V.; Valles, J.; Alvarez-Lerma, F.; Sierra, R.; Saavedra, P.; Alvarez-Salgado, F.; Group, C. S., Benefits of Minocycline and Rifampin-Impregnated Central Venous Catheters. Intensive Care Med. 2004, 30 (10), 1891-1899.
Osma, S.; Kahveci, Ş.; Kaya, F.; Akalm, H.; Özakm, C.; Yilmaz, E.; Kutlay, O., Efficacy of Antiseptic-Impregnated Catheters on Catheter Colonization and Catheter-Related Bloodstream Infections in Patients in an Intensive Care Unit. J. Hosp. Infect. 2006, 62 (2), 156-162.
Meyer, B.; Genoni, A.; Boudier, A.; Leroy, P.; Ruiz-Lopez, M. F., Structure and Stability Studies of Pharmacologically Relevant S-Nitrosothiols: A Theoretical Approach. The Journal of Physical Chemistry A 2016,120 (24), 4191-4200.
Pant, J.; Gao, J.; Goudie, M. J.; Hopkins, S.; Locklin, J.; Handa, H., A Multi-Defense Strategy: Enhancing Bactericidal Activity of a Medical Grade Polymer with a Nitric Oxide Donor and Surface-Immobilized Quaternary Ammonium Compound. Acta Biomater. 2017.
Liu et al., Covalent Grafting of Antifouling Phosphorylcholine-Based Copolymers with Antimicrobial Nitric Oxide Releasing Poly11n,irs lo Enhance Infection-Resistant Properties of Medical Device Coatings, Langmuir, Oct. 30, 2017, pp. 13105-13113.
International Search Report for PCT/US2-18/056778 dated Feb. 12, 2019.

* cited by examiner

NITRIC OXIDE-RELEASING ANTIBIOTICS, METHODS OF MAKING, AND METHODS OF USE

CROSS-REFERENCE TO RELATED APPLICATIONS

This application claims the benefit of and priority to U.S. Provisional Application Ser. No. 62/893,897, having the title "NITRIC OXIDE-RELEASING ANTIBIOTICS, METHODS OF MAKING, AND METHODS OF USE", filed on Aug. 30, 2020, the disclosure of which is incorporated herein by reference in its entirety.

BACKGROUND

Bacteria will often transition between a free living, planktonic state and a robust biofilm. Biofilms are bacteria that have encased themselves in a protective hydrated matrix of polysaccharides and proteins and most commonly occur at implanted medical device interfaces. The longer these biomedical devices remain within the body, the higher the risk of infection and formation of these biofilms. These biofilms often lead to chronic inflammation and tissue damage to the affected area. This ultimately leads to increased healthcare costs and discomfort to patients that require these types of long-term implanted devices that are highly prone to infection. Once formed, the administration of antibiotics at hundreds to thousands of times higher than the minimum inhibitory concentration (MIC) have been shown to have little effect on biofilms. One of the primary mechanisms for resistance is the limitation of antibiotic permeability through the matrix that is encapsulating the bacteria. This complex issue has led to the development of potential treatments to eradicate and prevent biofilm formation.

Despite advances in biofilm research, there is still a scarcity of compounds that are both potent and efficacious in combating and preventing biofilm-related infections. These needs and other needs are satisfied by the present disclosure.

SUMMARY

Embodiments of the present disclosure provide modified antibiotic compounds, methods of making modified antibiotic compounds, methods of use, products including modified antibiotic compounds, and the like.

An embodiment of the present disclosure includes a modified antibiotic compound comprising a nitric oxide release agent covalently attached to an antibiotic molecule.

An embodiment of the present disclosure also includes a method of making a modified antibiotic compound which includes covalently attaching a nitric oxide release agent to an antibiotic molecule. The attachment can be formed by mixing the nitric oxide release agent and the antibiotic molecule in a solvent to form a mixture, and nitrosating the mixture.

Another embodiment of the present disclosure includes a product with antimicrobial properties. The product includes a polymer material and a modified antibiotic compound, the modified antibiotic compound including a nitric oxide release agent covalently attached to an antibiotic molecule.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
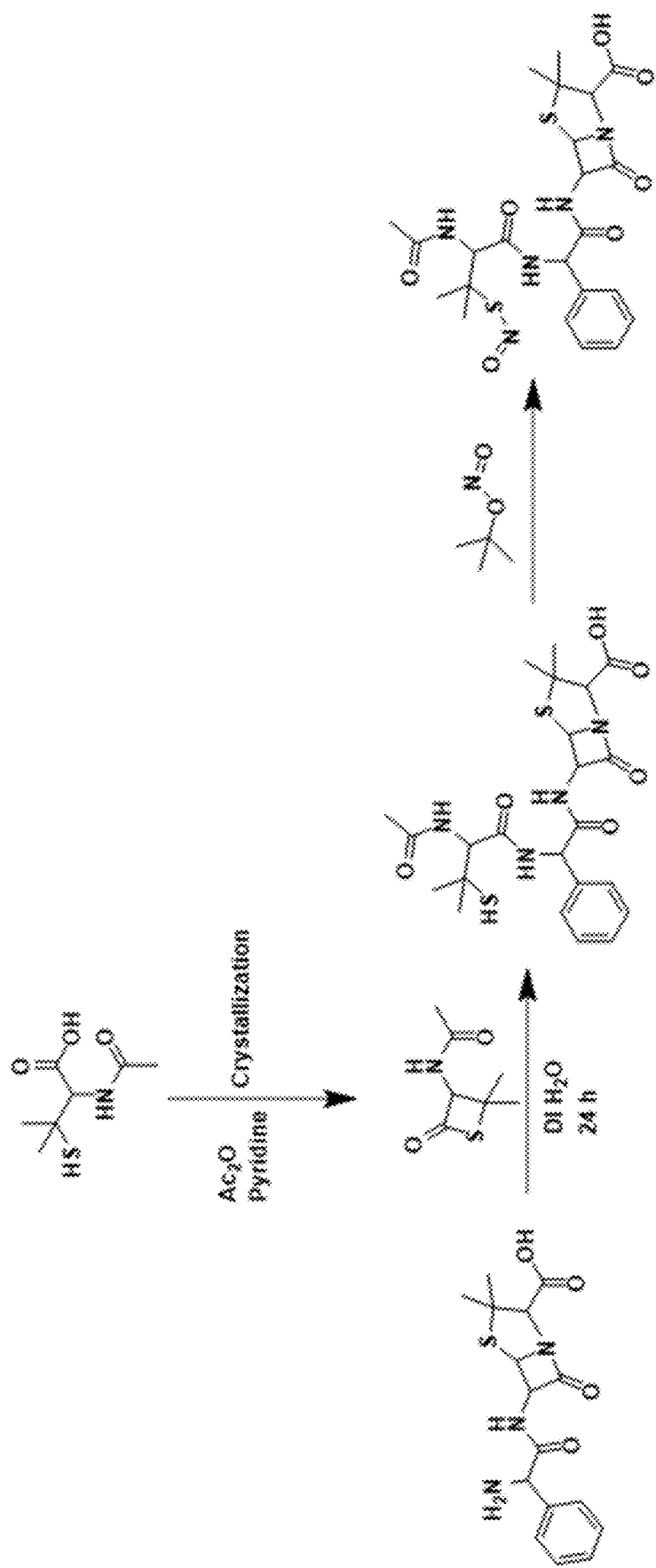
FIG. 1 is an example of SNAPicillin synthesis through the covalent attachment of SNAP by combining a self-protected NAP molecule with unmodified ampicillin and subsequent nitrosation using t-butyl nitrite according to embodiments of the present disclosure.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, biomedical engineering, and the like, which are within the skill of the art.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "reactive coupling group", as used herein, refers to any chemical functional group capable of reacting with a second functional group to form a covalent bond. The selection of reactive coupling groups is within the ability of the skilled artisan. Examples of reactive coupling groups can include, but are not limited to, primary amines (—$NH_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can also include thiol groups (—SH) and sulfhydryl reactive groups such as maleimides, haloacetyls, and pyridyl disulfides. Further examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphEnylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g. have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. Throughout the application, preferred alkyl groups are lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S-alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O— alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

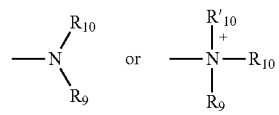

wherein $R_9$, $R_{10}$, and $R'_{10}$ each independently represent a hydrogen, an alkyl, an alkenyl, —$(CH_2)_m$—$R_3$ or $R_9$ and $R_{10}$ taken together with the N atom to which they are attached complete a heterocycle having from 4 to 8 atoms in the ring structure; $R_3$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In still other embodiments, the term "amine" does not encompass amides, e.g., wherein one of $R_9$ and $R_{10}$ represents a carbonyl. In additional embodiments, $R_9$ and $R_{10}$ (and optionally $R'_{10}$) each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

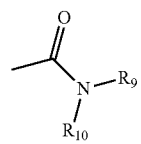

wherein $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, and —CN.

The term "carbonyl" is art-recognized and includes such moieties as can be represented by the general formula:

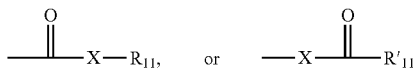

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "monoester" as used herein refers to an analogue of a dicarboxylic acid wherein one of the carboxylic acids is functionalized as an ester and the other carboxylic acid is a free carboxylic acid or salt of a carboxylic acid.

Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms are boron, nitrogen, oxygen, phosphorus, sulfur and selenium. Other heteroatoms include silicon and arsenic.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valences of the heteroatoms.

In various aspects, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, $-CN$, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

The term "copolymer" as used herein, generally refers to a single polymeric material that is comprised of two or more different monomers. The copolymer can be of any form, such as random, block, graft, etc. The copolymers can have any end-group, including capped or acid end groups.

The terms "mean particle size" and "average particle size," as used interchangeably herein, generally refer to the statistical mean particle size (diameter) of the particles in the composition.

The terms "mean pore size" and "average pore size," as used interchangeably herein, generally refer to the statistical mean pore size (diameter) of the pores in a porous material.

The terms "monodisperse" and "homogeneous size distribution", as used interchangeably herein, describe a population of particles or pores all having the same or nearly the same size. As used herein, a monodisperse distribution refers to distributions in which about 90% of the particles or pores in the distribution have a size that lies within about 5% of the mean size for the distribution.

As used herein, the term "linker" refers to a carbon chain that can contain heteroatoms (e.g., nitrogen, oxygen, sulfur, etc.) and which may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. Those of skill in the art will recognize that each of these groups may in turn be substituted. Examples of linkers include, but are not limited to, pH-sensitive linkers, protease cleavable peptide linkers, nuclease sensitive nucleic acid linkers, lipase sensitive lipid linkers, glycosidase sensitive carbohydrate linkers, hypoxia sensitive linkers, photo-cleavable linkers, heat-labile linkers, enzyme cleavable linkers (e.g., esterase cleavable linker), ultrasound-sensitive linkers, and x-ray cleavable linkers.

Abbreviations: NO, nitric oxide; SNAP, S-nitroso-N-acetylpenicillamine; NAP, N-acetyl-D-penicillamine; 3-Acetamido-4,4-dimethylthietan-2-one, NAP-thiolactone; LB, Luria broth; EDTA, ethylenediamine tetraacetic acid; CarboSil® 20 80A thermoplastic silicone-polycarbonate-urethane (hereafter will be referred to as CarboSil); THF, tetrahydrofuran; PBS, Phosphate buffered saline; ATCC, American Type Tissue Collection. GSNO, S-nitroso-glutathione; SIM, Surface immobilized; RSNO, S-nitrosothiol The terms "anti-fouling" or "anti-foul" as used herein, applies to compositions, surfaces, or articles having characteristics preventing or minimizing the adhesion of biological materials (e.g., proteins), microorganisms, or other debris.

The terms "antimicrobial" and "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent the growth or reproduction of the microorganism.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.* Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, Peptococcus species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydia trachomatis, Chlamydia psittaci, Coxiella burnetti, Escherichia coli, Neisserria meningitidis, Neisserria gonorrhea, Haemophilus influenzae, Haemophilus ducreyi,* other *Hemophilus* species, *Yersinia pestis, Yersinia enterolitica,* other *Yersinia* species, *Escherichia coli, E.* hirae and other *Escherichia* species, as well as other Enterobacteria, *Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae.*

The terms "broad-spectrum biocide", "biocide", and "biocidal" as used herein include, without limitation, pesticides (e.g. fungicides, herbicides, insecticides, algicides, molluscicides, miticides, and rodenticides) and antimicrobials as defined above and may also include germicides, antibiotics, antibacterials, antivirals, antifungals, antiprotozoals, and antiparasites.

The term "antimicrobial effective amount" as used herein refers to that amount of the compound being administered/released which will kill microorganisms or inhibit growth and/or reproduction thereof to some extent (e.g. from about 5% to about 100%). In reference to the compositions or articles of the disclosure, an antimicrobial effective amount refers to that amount which has the effect of diminishment of the presence of existing microorganisms, stabilization (e.g., not increasing) of the number of microorganisms present, preventing the presence of additional microorganisms, delaying or slowing of the reproduction of microorganisms, and combinations thereof. Similarly, the term "antibacterial effective amount" refers to that amount of a compound being administered/released that will kill bacterial organisms or inhibit growth and/or reproduction thereof to some extent (e.g., from about 5% to about 100%). In reference to the compositions or articles of the disclosure, an antibacterial effective amount refers to that amount which has the effect of diminishment of the presence of existing bacteria, stabilization (e.g., not increasing) of the number of bacteria present, preventing the presence of additional bacteria, delaying or slowing of the reproduction of bacteria, and combinations thereof.

As used herein the term "biocompatible" refers to the ability to co-exist with a living biological substance and/or biological system (e.g., a cell, cellular components, living tissue, organ, etc.) without exerting undue stress, toxicity, or adverse effects on the biological substance or system.

GENERAL DISCUSSION

In accordance with the purpose(s) of the present disclosure, as embodied and broadly described herein, embodiments of the present disclosure, in some aspects, relate to NO releasing antibiotic molecules.

In general, embodiments of the present disclosure provide for methods of making modified antibiotic compounds, compositions including modified antibiotic compounds, and products including modified antibiotic compounds.

The use of nitric oxide (NO) releasing materials has been a popular strategy to confront this issue of antibiotic resistant biofilms. In the body, NO is a versatile free radical molecule that facilitates a variety of physiological processes. It plays an important role in regulating blood pressure through vascular smooth muscle cell relaxation, preventing platelet activation on healthy endothelium, and is used by macrophages as a method to eliminate foreign pathogens. Due to its instability in a free radical state, the development of synthetic NO donating molecules has gained in popularity as a method to stabilize the molecule and provide a platform for localized NO release.

Two popular classes of NO donors that are widely used in this fashion are N-diazeniumdiolates (NONOates) and S-nitrosothiols (RSNOs). Using these donors, a wide variety of materials ranging from polyurethanes, silica nanoparticles, dendrimers, silicone rubber, and xerogels have been made significantly more biocompatible by demonstrating high antimicrobial capabilities. Specifically, the exogenous delivery of NO has been investigated as a means to kill antibiotic resistant bacteria and disperse highly resistant and robust biofilms into a more vulnerable planktonic state. This has led to the development of strategies that simultaneously deliver antibiotics with NO as dispersed biofilms become more vulnerable to traditional antibiotic treatments.

The highly beneficial function of utilizing exogenous sources of NO to disperse antibiotic resistant biofilms has been proven in multiple instances from recent studies. The primary mechanism for how NO promotes this dispersal pathway is its ability to increase the intracellular phosphodiesterase (PDE) activity of the biofilm, which ultimately increases the degradation rate of cyclic di-GMP, a messenger molecule directly related to maintaining biofilm integrity. This mechanism specifically switches the bacteria to a planktonic mode of growth, making them more vulnerable to traditional antibiotic treatments. The dispersal function of NO makes the dual administration of NO in combination with antibiotics a promising strategy for treating biofilms. Concentrations of NO as low as 450 pM have been shown to be able to trigger this dispersal mechanism and force biofilms into a planktonic state. However, these levels of NO might not be able to effectively kill the free-living bacteria that emerge, which can lead to further and more serious infection complications at different parts within the body. Embodiments of the present disclosure provide for methods and treatments that address these issues.

The present disclosure includes a modified antibiotic compound including a nitric oxide release agent covalently attached to an antibiotic molecule. Having a single molecule with the combined functionalities of both of a stable NO donor and an antibiotic can be a very efficient approach for combating and preventing biofilm related infections. Advantageously, the modified antibiotic compound of the present disclosure can have greater stability under physiological conditions than other molecules such as NONOates, resulting in prolonged NO release combined with potent antibiotic functionality.

Embodiments of the present disclosure include a modified antibiotic compound as above, wherein the modified antibiotic compound is included in a polymer material.

Methods of making the modified antibiotic compound are also described herein.

The modified antibiotic compound of the present disclosure can be a synthetic RSNO (e.g. S-nitroso-N-acetylpenicillamine (SNAP)) covalently attached to an antibiotic molecule (e.g. ampicillin) to create a novel dual functional antimicrobial agent, also referred to as a modified antibiotic compound. This is the first instance of utilizing RSNO chemistry in synergy with an antibiotic in the same molecule. In other embodiments, the nitric oxide release agent can be such as S-nitroso-glutathione, and S-nitroso-N-acetylcysteine, S-nitrosocysteine, S-nitrosopenicillamine, S-nitroso-B,D-glucose, S-nitrosocaptopril, S-nitrosocysteamine, and S-nitroso-3-mercapto-propanoic acid.

In some embodiments, the antibiotic molecule is ampicillin. In other embodiments, the antibiotic molecule can be vancomycin, gentamicin, cephalexin, and the like.

In some embodiments, the nitric oxide release agent and the antibiotic molecule can be mixed in an about an equimolar ratio. In other embodiments, the nitric oxide release agent and the antibiotic molecule can be mixed in about a 2:1 molar ratio.

In embodiments, the nitric oxide release agent is S-nitroso-N-acetylpenicillamine as described above. The modified antibiotic compound, when comprising SNAP and ampicillin is referred to herein as SNAPicillin. The terms "modified antibiotic compound" and "SNAPicillin" are intended to be used interchangeably, although "modified antibiotic compound" can also include other combinations of nitric oxide release agents and antibiotic molecules as can be appreciated by one of skill in the art.

In some embodiments, the modified antibiotic compound can be formed by covalently attaching a nitric oxide release agent to an antibiotic molecule. The attachment can be formed by mixing the nitric oxide release agent and the antibiotic molecule in a solvent then nitrosating the mixture. The nitrosation can occur through the excess addition of t-butyl nitrite or an acidified sodium nitrite solution to the mixture. The excess addition can be about 3 times molar excess of t-butyl nitrate with respect to the ampicillin quantity.

In some embodiments, the modified antibiotic compound of the present disclosure can be used for the treatment of a biofilm. In some embodiments, the biofilm can be present on a biomedical device. Advantageously, contacting a biofilm (e.g. a S. aureus adhered biofilm) with the modified antibiotic compound can reduce the viability of biofilm bacteria by about 99.8% or more, and bacteria dispersed in a planktonic state by about 99.3% or more. The combination of both a NO release agent and an antibiotic in the molecule described herein allows for the dispersal of biofilms while making them more susceptible to the antibiotic moiety. As described in greater detail in the Example below, the zone of inhibition against *S. aureus* of the modified antibiotic compound was compared to those of both traditional ampicillin and SNAP loaded polymer films. Advantageously, the zone of inhibition of the modified antibiotic compound described herein showed a larger area of bactericidal impact than that of either the antibiotic molecule or the NO release agent in isolation.

The present disclosure also provides for products with antimicrobial properties. The products can include a modified antibiotic compound as described above and a polymer material. In embodiments, the polymer substrate/polymer material can include polymers such as, but not limited to polyurethane, silicone, polyvinyl chloride, ketone polymers (including, but not limited to, polyether ether ketone), polyethylene (including, but not limited to, ethylene vinyl acetate), bioresorbable polymers (including, but not limited to, polylactic acid, polyglycolic acid, and polycaprolactone), fluoropolymers (including, but not limited to, polytetrafluoroethylene, perfluoroether, and fluorinated ethylene propylene), and combinations thereof.

In embodiments, the polymer substrate includes polymer materials typically used in the making of medical devices. In embodiments, the polymer material can be CarboSil.

In some embodiments, the modified antibiotic compound can be blended with the polymer material to form a polymer film. In some embodiments, the polymer material can be impregnated with the modified antibiotic compound. Advantageously, the modified antibiotic compound of the present disclosure is soluble in a large number of solvents (e.g. tetrahydrofuran, methanol, chloroform), which is not true for a large majority of existing antibiotics. As such, existing antibiotics have a limited ability to evenly disperse within polymer matrices when coated or impregnated within a bulk material, such as a polymer material described above.

In embodiments, the product including the polymer substrate can be a medical device or can form part of a medical device. The modified antibiotic compound can form a film on the polymer substrate or be blended in the polymer substrate to form the medical device or part thereof. Such products can include, but are not limited to catheters, IV delivery tubes, stents, blood and urinary catheters, PICC lines, feeding tubes, wound dressings, extracorporeal circuits, membrane oxygenators, vascular grafts, endotracheal tubes, and the like.

Examples

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Traditional methods for addressing infections related to medical devices with antibiotic treatments has been growing more ineffective as complications with biofilms and resistant bacteria at the material interface become more prevalent. In this project, S-nitroso-N-acetylpenicillamine (SNAP), a common S-nitrosothiol (RSNO) used for controlled nitric oxide (NO) release, was combined with ampicillin into one multifunctional molecule to provide additional bactericidal properties for modifying drug-delivering polymers. The SNAP functionalized ampicillin (SNAPicillin) was physically blended into a hydrophobic silicone polycarbonate-urethane copolymer (CarboSil) and maintained its antibiotic properties while simultaneously releasing a steady flux of NO compared to traditional SNAP impregnated polymers. For zone of inhibition tests, the SNAPicillin blended polymers were compared to ampicillin and SNAP blended polymers to ensure the ampicillin functionality of the molecule is maintained. *Staphylococcus aureus* (*S. aureus*) biofilms were grown on polymer films to test the dispersive effects of NO while simultaneously forcing the bacteria into a planktonic state for increased susceptibility to the antibiotic moiety. The synthesized SNAPicillin was able to reduce the viability of *S. aureus* as both an adhered biofilm by 99.9±0.18% and the resulting bacteria dispersed in a planktonic state by 99.5±0.264%.

Materials and Methods

Materials:

N,N-dimethylformamide-d7, tetrahydrofuran, ethanol, methanol, N-acetylpenicillamine, t-butyl nitrite, chloroform, pyridine, acetic anhydride, hydrochloric acid, sulfuric acid, hexanes, and anhydrous magnesium sulfate were purchased from Sigma Aldrich (St. Louis, Mo.). Sodium ampicillin was purchased from Gold Biotechnology (St. Louis, Mo.). CarboSil 2080A (from here on referred to as CarboSil) was obtained from DSM Biomedical Inc. (Berkeley, Calif.). Gram-positive *S. aureus* (ATCC 6538) was obtained from American Type Culture Collection (Manassas, Va.). LB agar and Luria Broth were both obtained from Fischer Bioreagents (Fair Lawn, N.J.).

SNAPicillin Synthesis:

Covalent attachment of SNAP to ampicillin was done through the reductive amination reaction with self-protected N-acetyl penicillamine thiolactone molecule (FIG. 1). Synthesis of (3-Acetamido-4,4-dimethylthietan-2-one) (NAP-thiolactone) has been described previously.[22] Briefly, 5 g of NAP was first dissolved in 10 mL of pyridine and chilled. A separate container consisting of 10 mL of pyridine and 10 mL of acetic anhydride was also chilled as well. The two components were then mixed together and allowed to stir overnight. The solution then had the pyridine removed via rotary evaporation at 60° C. and was allowed to cool to room temperature before being dissolved in 20 mL of chloroform. The resulting solution was then washed and extracted three times with 1M HCl followed by being dried over anhydrous magnesium sulfate. The chloroform was removed with rotary evaporation at room temperature and then washed thoroughly with hexanes. The resulting crystalline white powder was dried under vacuum at room temperature overnight.

For NAP attachment to ampicillin, ampicillin was first dissolved in deionized water and an equimolar amount of NAP-thiolactone was added. The reaction was allowed to stir for 48 h at room temperature under inert gas. After NAP attachment, nitrosation was done by adding excess t-butyl nitrite to the stirring solution for 30 min. T-butyl nitrite was first chelated of any metal ion contaminants and stabilizers by washing thoroughly with an aqueous solution of 25 mM cyclam. The nitrosated SNAPicillin product will precipitate as the reaction progresses. The precipitated product is then filtered, rinsed with chilled deionized water to remove any unreacted ampicillin, followed by an ethanol rinse, and then dried under vacuum at room temperature overnight before being stored at −20° C.

SNAPicillin Characterization

NMR Characterization $^1$H NMR data of ampicillin and its conversion to SNAPicillin was analyzed using a Varian/Agilent mercury spectrometer (300 MHz, DMF-d7, δ).

Degree of Conjugation

Attachment of NAP-thiolactone to the free primary amine of ampicillin was quantified using Ellman's test for thiols.[23] Briefly, a stock solution of 2 mM 5,5'-dithio-bis(2-nitrobenzoic acid) (DTNB) and 50 mM sodium acetate in deionized water was prepared. Weighed portions of NAP-ampicillin were then dissolved in a separate solution of deionized water. The working reagent was then prepared by adding 50 μL of the DTNB solution, 100 μL of Tris buffer (1M, pH=8.0), 840 μL of deionized water, and 10 μL of the NAP-ampicillin solution. The solution was then allowed to incubate at room temperature for 15 minutes before measuring the optical absorbance at 412 nm using a Genesis 10S UV-vis spectrophotometer. Molarity of thiol functionality is done by dividing the absorbance by the extinction coefficient of the reagent (13600 $M^{-1}$ $cm^{-1}$). Cysteine was used as a standard for calibration for all Ellman's assay studies.

Nitrosation efficiency of the exposed thiol group was quantified by catalytically exhausting the NO in the SNAPicillin. Aqueous solutions of SNAPicillin of known molarity were prepared and 25 μL injections of the solution were placed into an amber reaction vial containing 30 μL of 50 mM $CuCl_2$, 1.5 μL of 10 mM cysteine, and 2945 μL of PBS. The NO exhausted from the SNAPicillin was then quantified using a Sievers 280i Nitric Oxide Analyzer (NOA) and compared to the theoretical amount of SNAP attachment.

Leachate

Leaching of SNAPicillin and SNAP was done by first blending equimolar amounts of the corresponding chemical (33.33 μmol $mL^{-1}$) into solutions of CarboSil dissolved in THF (50 mg $mL^{-1}$) and subsequently cast into Teflon molds to dry overnight. The dried films were then weighed and measured before being submerged into PBS. Quantification of SNAP leaching into solution was done by measuring absorbance at 340 nm via UV-vis analysis.

Ampicillin eachate from CarboSil films was done by making polymer solutions with equimolar amounts of SNAPicillin and ampicillin. Ampicillin was first dissolve in a small amount of methanol before being added to CarboSil in THF solutions and then solvent casted into Teflon molds. Films were then weighed and immersed in PBS containing EDTA. Quantification of ampicillin leaching into solution was done via the oxidation reaction with alkaline potassium permanganate following a previously established protocol.[24]

NO Release Kinetics

Real time NO release was measured using a Sievers 280i NOA (Nitric Oxide Analyzer). Polymer films containing SNAPicillin or SNAP were immersed in amber reaction vessels containing PBS (pH 7.4) with 100 μM EDTA to chelate any metal ion contaminants within the buffer. Solutions were continuously purged with a nitrogen sweep gas and bubbler to carry the NO from the solution directly to the NOA. In a separate NO releasing study, solutions containing 500 μM of either SNAPicillin or SNAP in PBS with EDTA were also tested under physiological conditions to obtain the stabilized NO release profile to compare passive release kinetics.

Bacteria Studies

Zone of Inhibition Assay

Zone of inhibition (ZOI) testing was done on polymer films containing the same composition of either ampicillin, SNAP, or SNAPicillin used in the leachate and NOA studies. A standard agar diffusion protocol was followed and tested against *S. aureus*. A single colony of bacterium was suspended into LB and incubated at 37° C. for 14 h while being rotated at 150 rpm. The optical density of each bacterial culture was then measured at 600 nm using a UV-Vis spectrophotometer. The observed optical density was adjusted to $1\times10^7$ colony forming units per mL using a standard calibration curve of each corresponding bacteria. A sterile cotton swab was then used to dip into each culture media and spread onto premade LB-agar petri dishes. The polymer films of either ampicillin, SNAP, SNAPicillin, along with controls (diameter: 8 mm, thickness: 200 μm) were then placed on top of the petri dishes and allowed to incubate overnight at 37° C. The ZOI was then measured and compared the following day to observe the antimicrobial effects of synthesized SNAPicillin molecule within a hydrophobic matrix.

Biofilm Dispersal Assay

Biofilms were grown for 48 h on circular CarboSil polymer films fabricated with a surface area of 1 $cm^2$. Solutions of *S. aureus* were prepared by placing one colony of bacteria in Luria Broth and incubated at 37° C. until the solution reached approximately $10^6$ to $10^8$ CFU $mL^{-1}$. Each polymer film was suspended in 2 mL of the bacteria solution and the solution was replenished with a fresh bacteria solution at 24 h of incubation. For the duration of the study the samples were incubated on a shaker at 150 rpms. After 48 h, the films were removed from the bacteria solutions and each film was gently rinsed with 5 ml of sterile PBS to remove any planktonic bacteria. The films were next incubated with 1 mL their specified test solutions and each solution type was tested at n=4. Each test solution was prepared with sterilized PBS and calculated to contain either 500 μM of ampicillin, SNAP, or SNAPicillin. After 24 h, the polymer films were removed from the test solutions, gently rinsed with PBS to remove planktonic bacteria, and homogenized in sterile PBS to remove any viable bacteria from the biofilm. The collected bacteria were serially diluted, plated on LB agar, and incubated for 18 h to achieve countable CFUs for comparison. A similar procedure was then done for the planktonic bacteria suspended in the solution of the incubated films to observe viable bacteria that shed from the potentially dispersed biofilms.

Results and Discussion

Synthesis and Characterization of Covalent Bound SNAP to Ampicillin

The synergistic effect of NO and antimicrobial treatments has been explored in the past as the administration of NO has been demonstrated to make biofilms more susceptible to other therapeutics such as antimicrobial peptides, polyamidoamine dendrimers, and silver sulfadiazine.[15, 25-26] While these types of studies give insight into how the combination of NO with antibiotics is a strong potential strategy for addressing resistant strains of bacteria, the simultaneous delivery of both molecules can potentially be difficult in a clinical setting. By directly attaching the NO releasing SNAP moiety directly to the antibiotic itself, it allows for an immediate interaction of both components and their methods of action in combatting bacteria. A combination using N-diazeniumdiolates (NONOates), another popular class of NO donor, in combination with ciprofloxacin has also been examined in eradicating *Pseudomonas aeruginosa* biofilms.[27] One of the key benefits of using an RSNO attached antibiotic over NONOates is its stability under physiological conditions. Popular RSNOs such as SNAP and GSNO have stable release kinetics when under physiological conditions while NONOates display more of a burst release. Thus, the use of RSNO's allows for prolonged and consistent elution of NO from SNAP containing compounds, in comparison. By covalently attaching SNAP to the common broad spectrum antibiotic, ampicillin, to form a completely novel NO donor (SNAPicillin), NO release can be prolonged for a variety of applications while still sustaining potent antibiotic functionality. Since only low levels of NO are necessary for effectively dispersing biofilms, the high release from NONOates is unnecessary for these types of applications. This allows for potential biomedical devices to incorporate SNAPicillin with the expectation of an extended lifetime in terms of antimicrobial capabilities.

Figure 2:
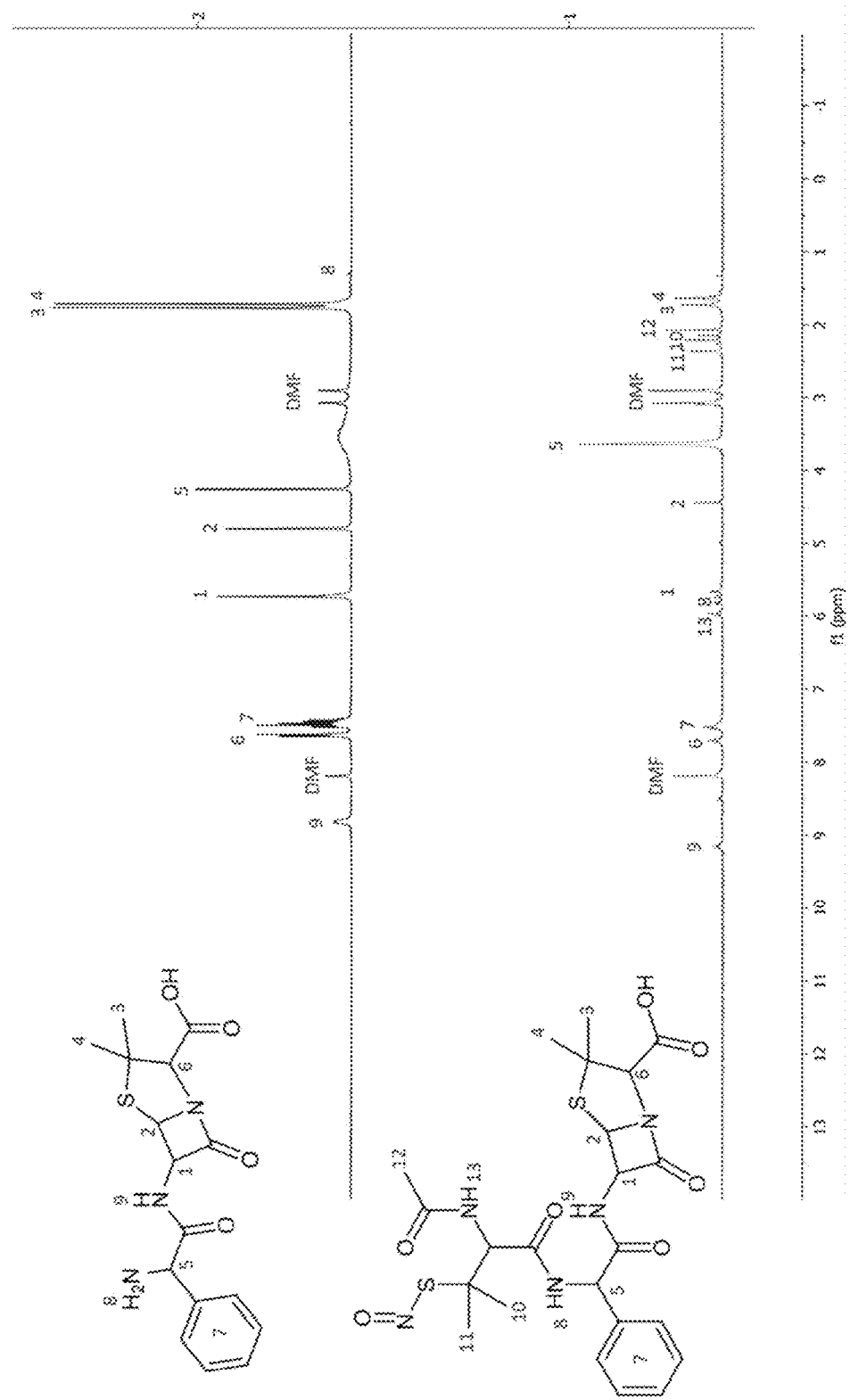
FIG. 2 provides a $^1$H NMR spectra of ampicillin (top) and SNAPicillin (bottom) with appropriately labeled hydrogen peaks.

Verification of key functional groups after the covalent attachment of SNAP to ampicillin was done using NMR (FIG. 2). Important functional groups are noted on the spectra with respect to the chemical structure, indicating a successful ring opening reaction off the NAP-thiolactone to the reactive amine site on the ampicillin molecule. Quantification of the conversion of ampicillin to SNAPicillin was done through several steps. The initial NAP-thiolactone ring opening reaction to the free primary amine site was quantified through detection of thiol functional groups using Ellman's Reagent (DTNB). Using this assay, conversion of primary amine sites to NAP functional groups was found to be 61.7±0.71%. A primary cause for not achieving a higher percentage is most likely due to steric hindrance of the NAP-thiolactone ring with the ampicillin primary amine. The amine on the ampicillin is attached to a carbon that is branched to an aromatic ring and carbonyl group, which gives the functional group a much lower degree of nucleophilicity. Once NAP was successfully attached, the molecule was then nitrosated with excess t-butyl nitrite and the nitrosation efficiency was quantified by catalytically breaking the sulfur-nitroso bond using a solution of copper (II) chloride and L-cysteine. The conversion of thiols to nitrosothiol groups was found to be 98.7±1.45%, demonstrating high nitrosation efficiency of the NAP functionalized product.

Figure 3A:
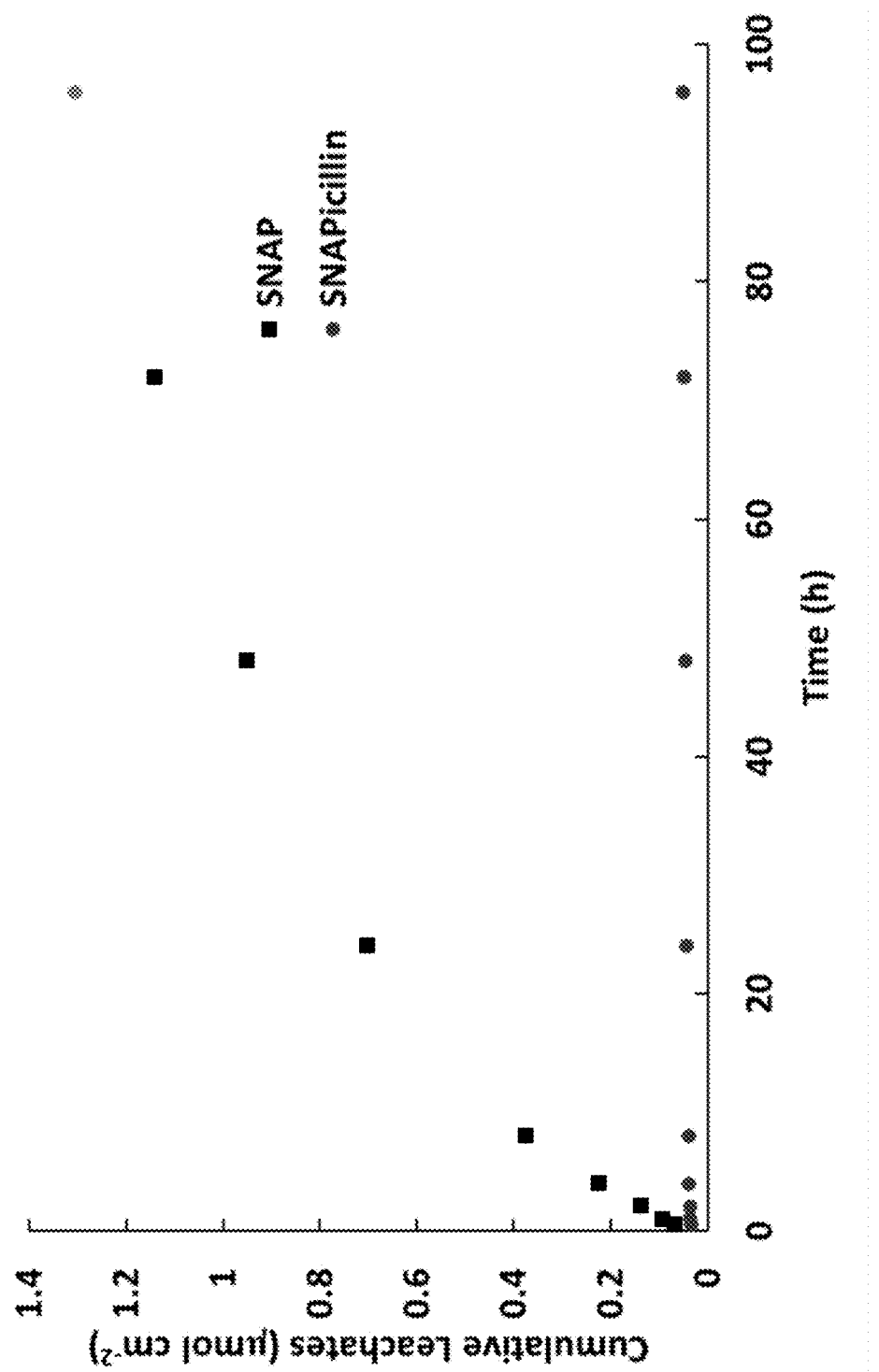
FIGS. 3A-3B show cumulative leachates of SNAP/SNAPicillin (top) and ampicillin/SNAPicillin (bottom) from CarboSil films blended with their corresponding component over 96 h while being kept in PBS at 37° C., in accordance with embodiments of the present disclosure.
Figure 3B:
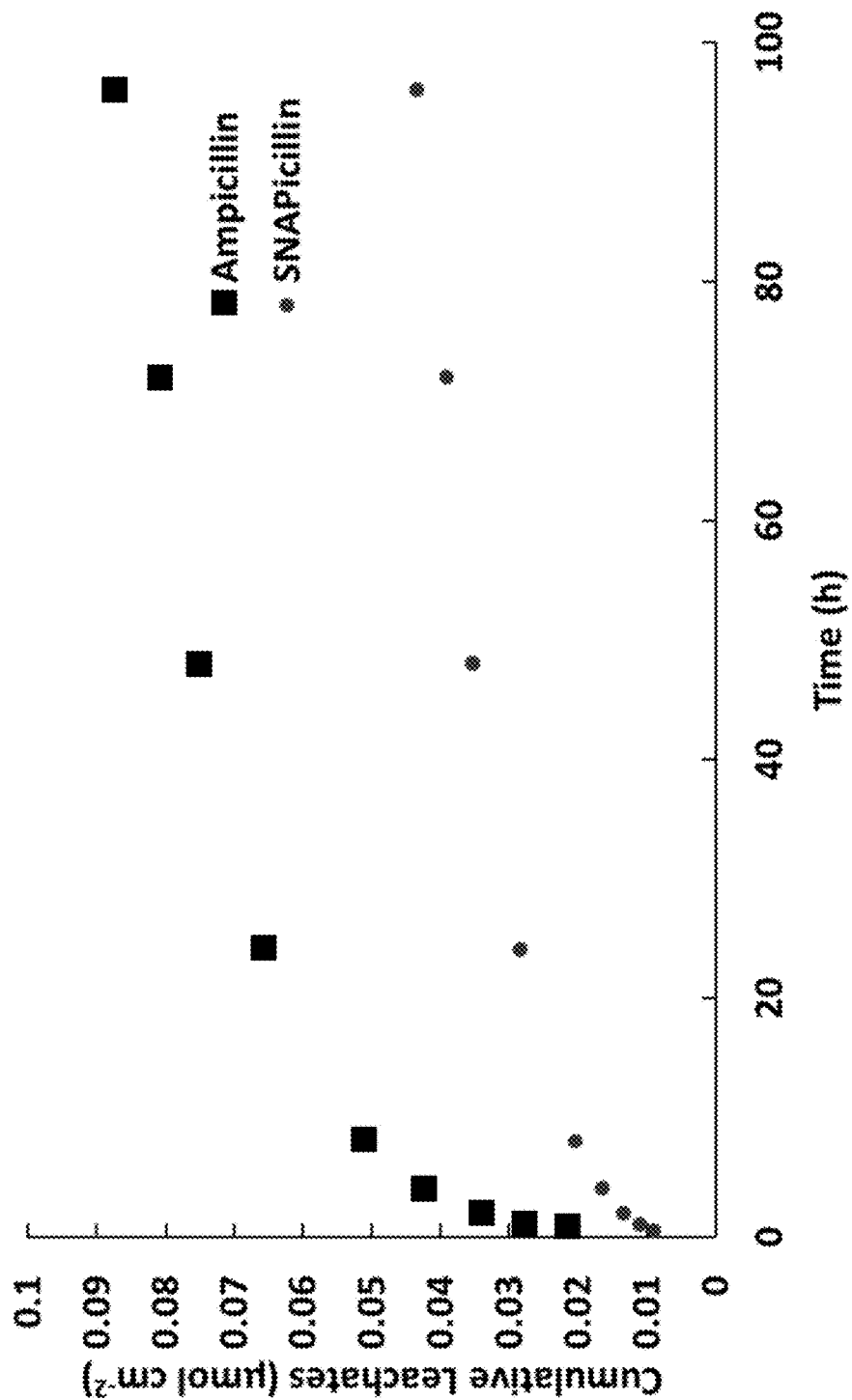

One issue holding back using the direct administration of NO donors as an effective therapeutic is its short half-life. To address this, a common method for controlling and directing the NO release of a donor in a localized and targeted area is to encapsulate it within a polymer. This strategy is also used for antibiotics and antiseptics as well, as catheters have been fabricated with physically blended drugs to combat and prevent infection.[28-30] One key advantage for modifying the ampicillin with SNAP was its change in solubility. A large majority of antibiotics are not soluble in organic solvents, limiting its ability to evenly disperse within polymer matrices when coated or impregnated within the bulk material. The attachment of SNAP allowed SNAPicillin to be soluble in a large number of organic solvents, expanding its uses within the medical device field. While these drug encapsulated polymers allow for effective localized antibiotic activity, leaching of the blended drug at an accelerated rate could dramatically reduce the antimicrobial lifetime of these devices by exhausting the drug reservoir within the polymer. To examine this, SNAPicillin was blended into a silicone rubber-polyurethane copolymer, CarboSil, and leaching was compared to both SNAP and ampicillin blended films over the course of 4 days. The polymer films were measured and weighed before being immersed in PBS at 37° C. and were periodically taken out to examine either SNAP or ampicillin leachates (FIGS. 3A-3B). The polymer films with blended SNAPicillin demonstrated significantly less overall leaching when compared to SNAP or ampicillin alone, making it a better alternative to incorporate into polymeric biomaterials for improving the biocompatibility of long term implanted medical devices. By the end of the 4 day SNAP leaching study, SNAPicillin blended films leached 0.051±0.10 µmol cm-2 while SNAP films leached 1.307±0.536 µmol cm-2. The ampicillin study displayed a similar amount of SNAPicillin leaching from films seen in the SNAP study, leaching 0.043±0.003 µmol cm-2 compared ampicillin films leaching 0.087±0.003 µmol cm$^{-2}$. The lower leaching amount is most likely due to the larger molecular size of SNAPicillin, especially when compared to SNAP.

Nitric Oxide Release Kinetics

Figure 4:
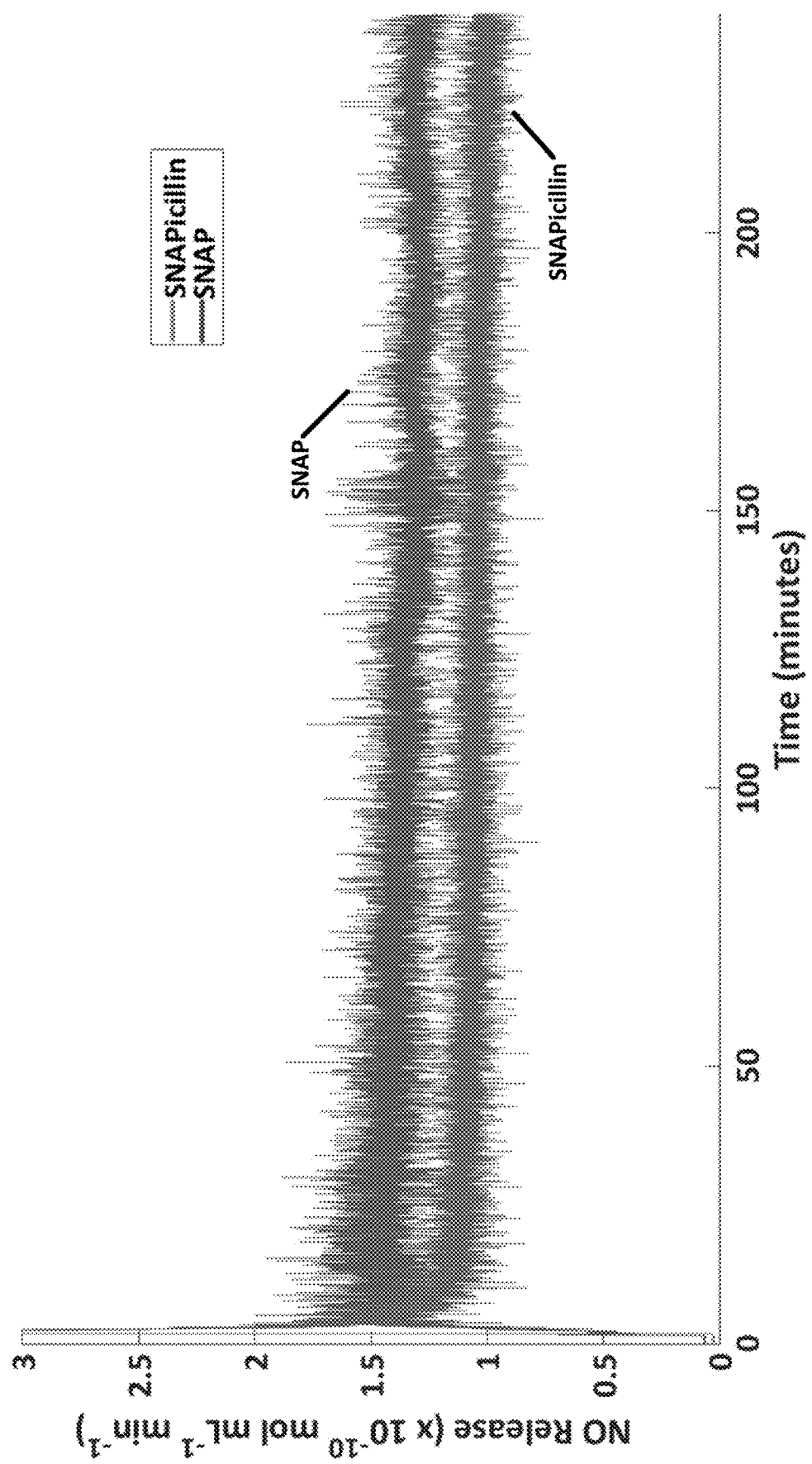
FIG. 4 demonstrates stabilized nitric oxide release kinetics from 500 µM solutions containing SNAP (blue/top) and SNAPicillin (orange/bottom) in PBS at 37° C. over the course of 4 h.

The NO release of the synthesized SNAPicillin was compared to pure SNAP by dissolving equimolar (500 µM) amounts of each into separate solutions of PBS (pH 7.4) containing 0.01 mM EDTA and placing them in an amber reaction vial submerged within a water bath at 37° C. while NO release was monitored in real time. Nitrogen gas was used to continuously purge the solution to examine the stabilized, passive release under these conditions. The solutions of SNAP were able to level off at a slightly higher rate of NO release than SNAPicillin solutions (FIG. 4). Although equimolar amounts of each component were used, the RSNO component on the SNAPicillin appears to be less reactive when compared to pure crystalline SNAP under physiological conditions. This follows a general trend in RSNO reactivity where larger molecules have increase intramolecular interactions that increase the overall stability of the compound.[31] This demonstrates that SNAPicillin has the potential to prolong the NO release duration as an administered solution and when incorporated into polymer matrices.

Figure 5:
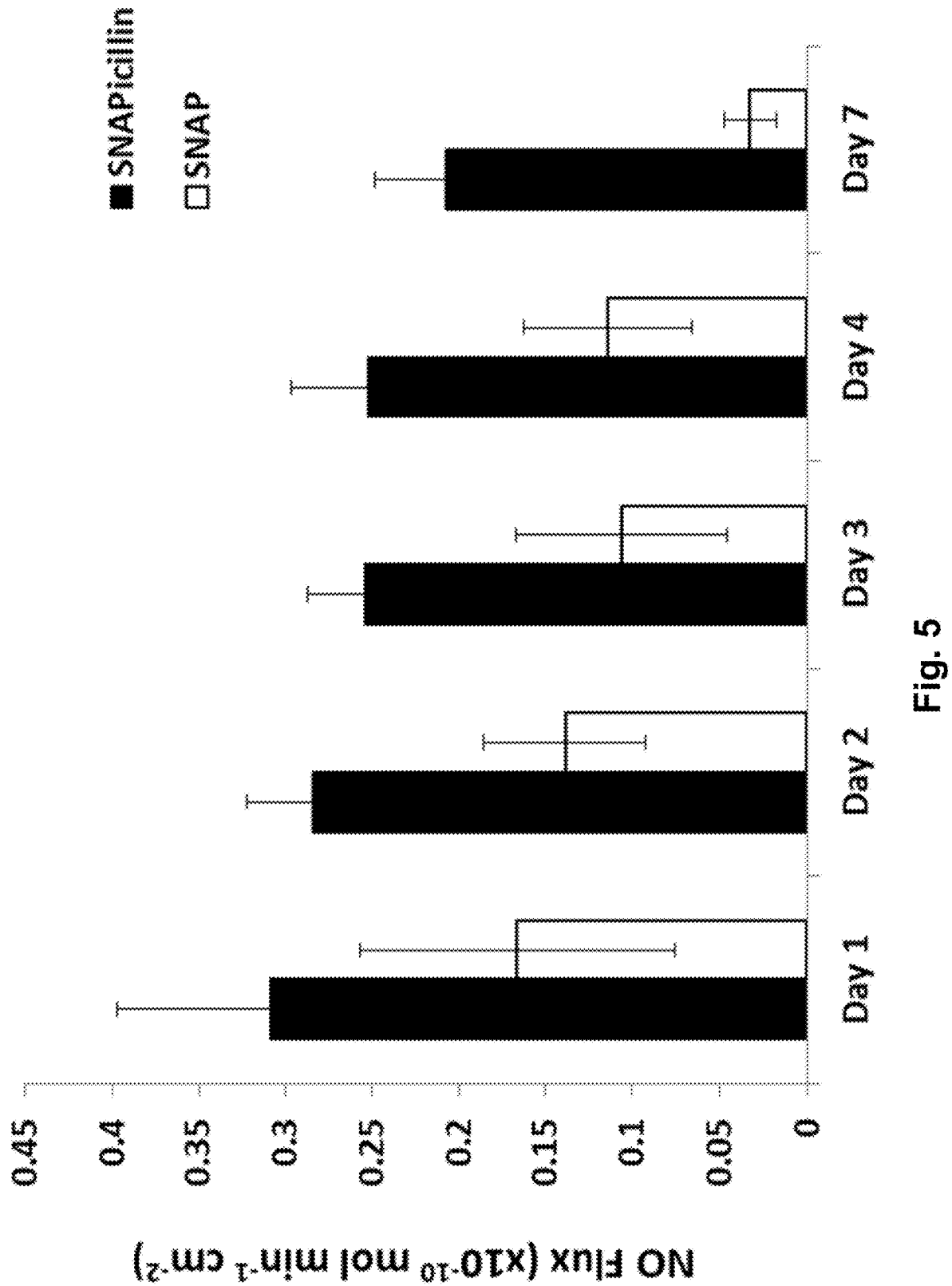
FIG. 5 is a graph illustrating nitric oxide release of CarboSil polymer films containing equimolar amounts of either SNAPicillin or SNAP over the course of 7 days in PBS at 37° C., in accordance with embodiments of the present disclosure.

A separate NO release study was also done by physically blending equimolar amounts into solutions of CarboSil, and solvent casting a thin polymer film to be analyzed. Since polymer films blended with SNAP are a common strategy to create a surface with controlled, localized NO release, a comparison of NO release was done using SNAPicillin containing polymer films to examine its potential as an alternative novel NO donor. The fabricated films were placed in PBS (pH 7.4) containing 0.01 mM EDTA at 37° C. to observe the real time NO releasing kinetics. The release trends for both blended donors were monitored over the course of 7 days and are shown in FIG. 5. Surprisingly, SNAPicillin blended films leveled off at higher NO fluxes at every time point when compared to SNAP. This is contrary to the pure solutions that were previously placed under physiological conditions, where SNAP was able to have a higher initial release. The difference is most likely is due to the leaching rate of either SNAP or SNAPicillin from a hydrophobic polymer matrix. As demonstrated from the earlier leaching study, SNAPicillin was able to be more securely embedded within the polymer matrix when compared to SNAP due to its increased molecular size, which directly corresponds to the demonstrated NO release kinetics.

The amount of NO donor remaining in the films was also quantified using UV-VIS after this time period to examine the potential release beyond the recorded 7 days. By the end of the NOA study, 21.9±1.72% of SNAPicillin was remaining within the CarboSil polymer films while the SNAP blended films were nearly exhausted of their reservoir displaying only 0.25±0.17% of SNAP remaining. As mentioned previously, due to the larger molecular weight of SNAPicillin, it was able to stay within the CarboSil matrix for a longer period of time when compared to SNAP blended films. This further emphasizes the versatility of the SNAPicillin donor as a possible RSNO donor substitute for NO releasing polymers that require sustained or controlled release kinetics with the additional antimicrobial functionality.

Antimicrobial Properties of SNAPicillin

Figure 6:
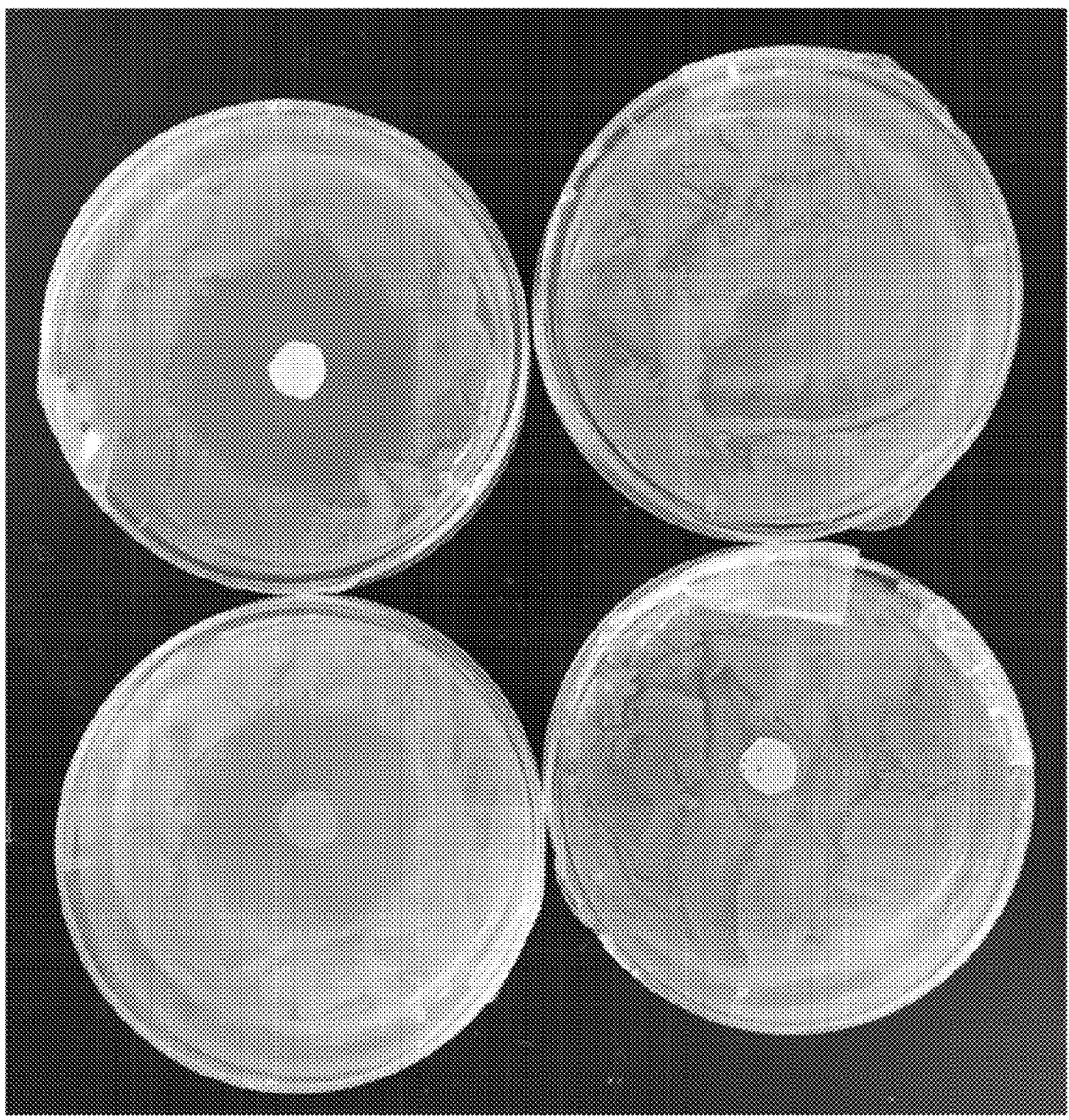
FIG. 6 is a camera image showing a zone of inhibition of CarboSil films with blended SNAPicillin (top left), SNAP (bottom left), or ampicillin (top right) compared to control CarboSil (bottom right) against *S. aureus*.

A significant advantage of using targeted antibiotics over NO releasing polymers is seen in its ability to prevent bacteria growth. Antibiotics such as ampicillin have demonstrated significant growth-inhibiting effects against targeted bacteria. To ensure the SNAP attachment to ampicillin was not interfering with this targeted potency, a zone of inhibition (ZOI) test against S. aureus was done. FIG. 6 demonstrates the effectiveness of blending either SNAP, ampicillin, or SNAPicillin within CarboSil polymer films (8 mm diameter) to inhibit bacterial colony formation using the same concentration as previously stated in the NOA and leachate studies. Due to the high reactivity of the free radical NO molecule, it is unable to diffuse well within the medium, which corresponds to the SNAP blended films only killing bacteria directly in contact with the film. This trend has been seen in the past with NO releasing hydrophobic polymers, where the ZOI is extremely limited beyond the interface of the polymer itself.[32]

The characterization of covalent attachment of SNAP was verified through FTIR (Fourier Transform Infrared Spectroscopy) and NMR (Nuclear Magnetic Resonance Spectroscopy) and its NO releasing characteristics were compared to pure, unmodified SNAP. The combination of both NO and ampicillin in one unique compound allows for the dispersal of biofilms while making them more susceptible to the antibiotic moiety. The zone of inhibition against S. aureus of the modified antibiotic compound was compared to those of both traditional ampicillin and SNAP loaded polymer films. Biofilms of S. aureus were grown onto films of CarboSil, a biocompatible copolymer comprised of polycarbonate-urethane with silicone, and treated with the solutions of synthesized SNAPicillin to observe its ability to disperse the biofilm and eliminate planktonic bacteria. Usually extremely high levels of NO are required to begin to see even the slightest inhibition around the polymer films, which at times can be cytotoxic towards mammalian cells as well. However, the ZOI values against S. aureus were 34.0±1.40 mm for SNAPicillin and 34.5±1.50 mm for ampicillin. This shows how by functionalizing the free primary amine of ampicillin with SNAP does not significantly inhibit its antimicrobial capabilities. It also expands the possibilities for using SNAPicillin as a potential topical agent to assist devices or wound healing materials that are in direct contact with tissue that are prone to infection.

Figure 7:
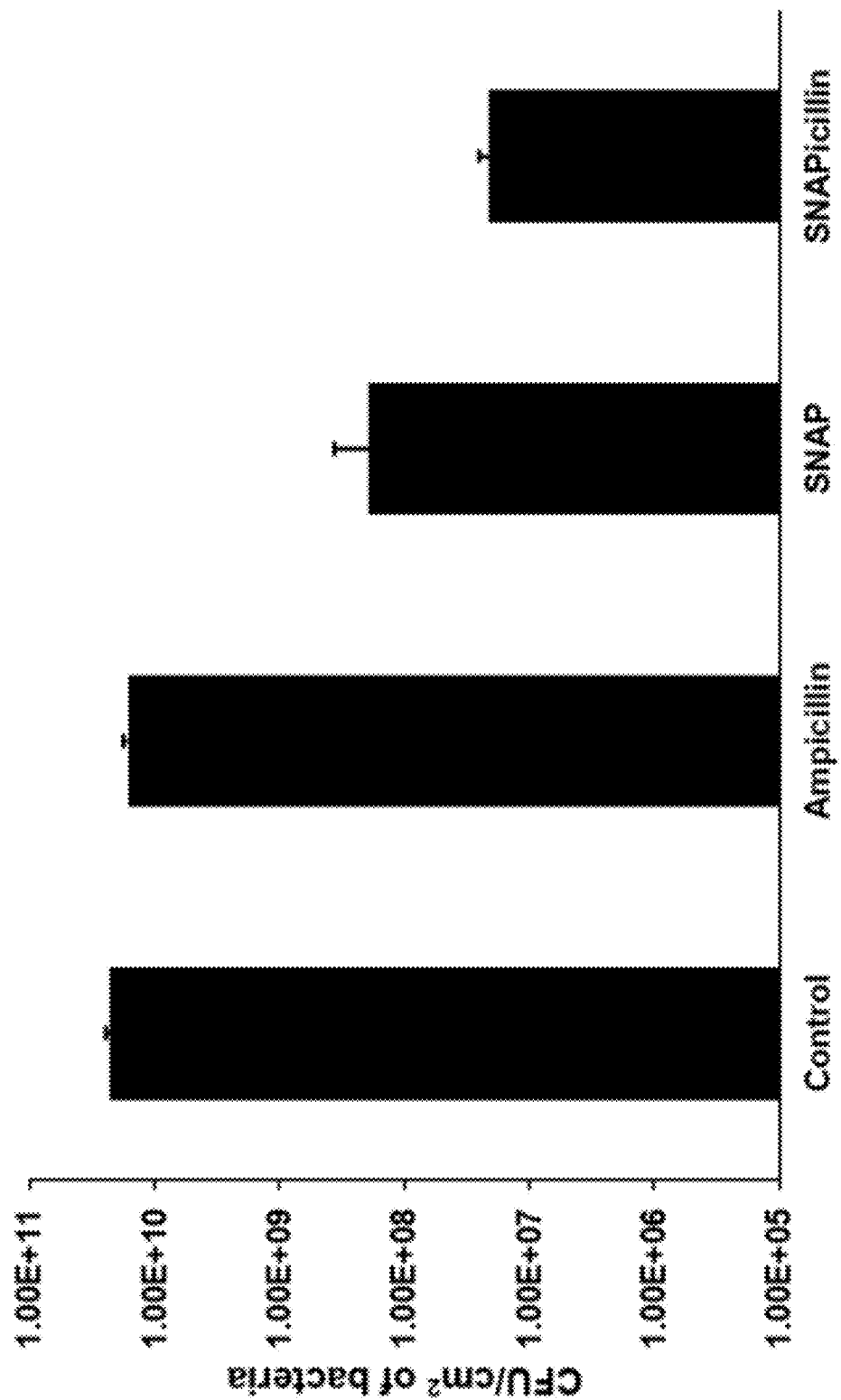
FIG. 7 is a graph of biofilm adhesion remaining on 48 h old preformed *S. aureus* biofilms onto CarboSil polymer films after being treated with 500 µM of the specified antimicrobial agent, in accordance with embodiments of the present disclosure.
Figure 8:
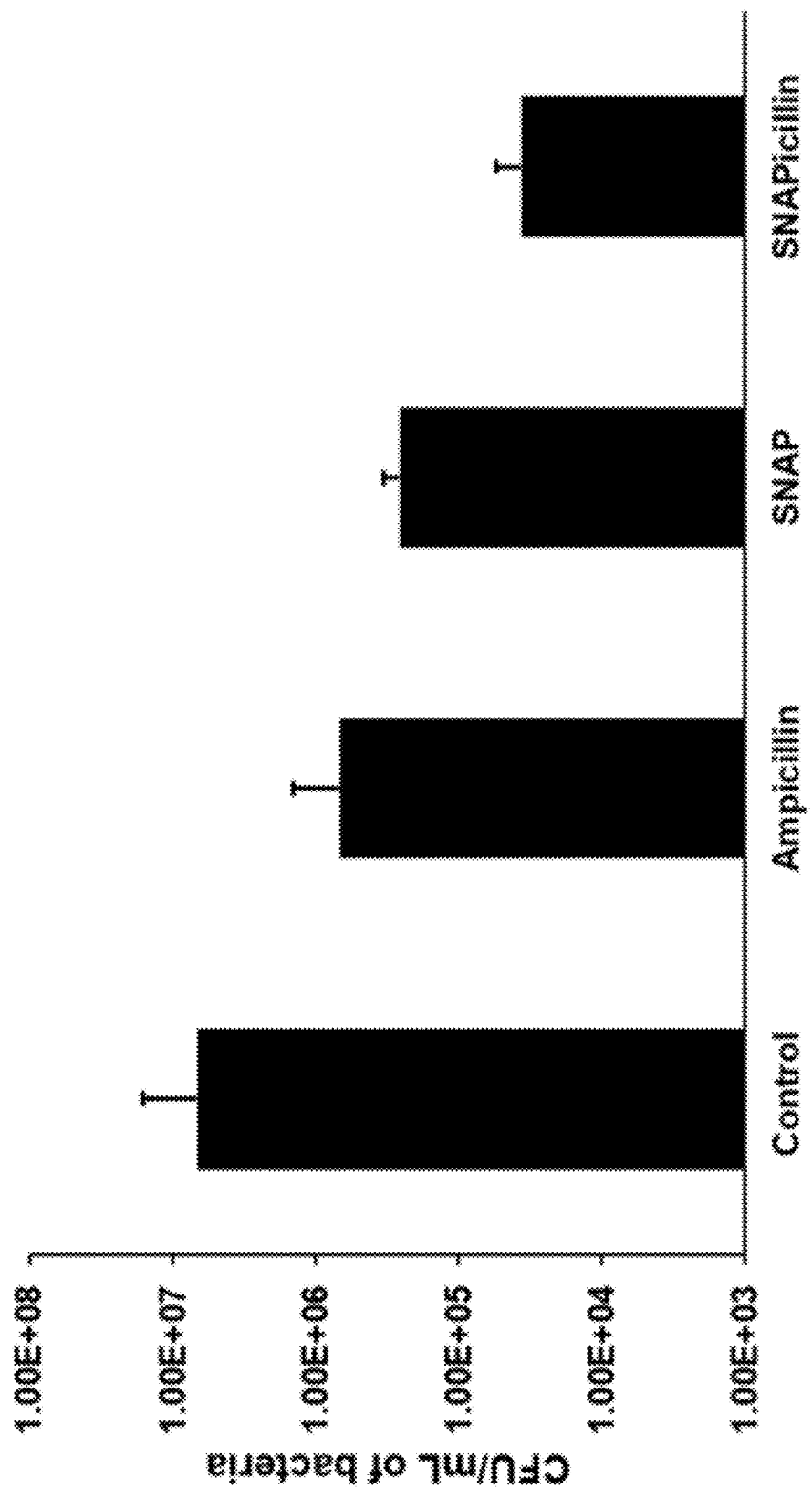
FIG. 8 is a graph illustrating planktonic bacterial viability from solutions containing CarboSil polymer films containing 48 h old preformed *S. aureus* biofilms after being treated with 500 µM of the specified antimicrobial agent.

While NO release from SNAP may have difficulties diffusing through agar for disk diffusion testing, it is extremely potent at dispersing biofilms. Antibiotics demonstrate little to no effect when treating these types of infections, often requiring concentrations up to a thousand times higher than traditional therapeutic administrations. To establish that the biofilm dispersal activity of the SNAPicillin is comparable to traditional NO releasing SNAP, S. aureus was allowed to form robust biofilms onto CarboSil polymer films over the course of 48 h. The polymer films were then immersed into solutions containing either ampicillin, SNAP, or SNAPicillin at a concentration of 500 µM and the adhered bacteria remaining on the film as well as the planktonic bacteria within the solutions were observed (FIGS. 7 and 8). Both SNAP and SNAPicillin demonstrated high antimicrobial potential in dispersing the biofilms, removing 99.2±0.762% and 99.9±0.18% of viable bacteria on the films respectively. As shown earlier, the SNAP solutions were able to passively release slightly more NO than the SNAPicillin solutions at equal concentrations, indicating that the synthesized SNAPicillin molecule has other biofilm dispersal mechanisms that are working in synergy with its NO release. As expected, the ampicillin solution was unable to penetrate the biofilm and only displayed a 28.9±5.89% reduction in bacterial viability. Even the planktonic bacteria in solution still showed some resistance against the ampicillin, demonstrating the robustness of the bacteria being shed off from the biofilms. The reduction in planktonic bacteria was only 90.0±1.13% for the pure ampicillin solution and 96.2±1.15% for SNAP, while SNAPicillin was able to demonstrate a 99.5±0.264% reduction. A similar trend was seen in a previous study where biofilms cells that were shed into solution displayed less antibiotic susceptibility compared to traditionally grown bacteria.[15] This puts more emphasis into the synergy of the combined antimicrobial activities utilized from SNAPicillin for both dispersing biofilms and eradicating any potential resistant planktonic bacteria.

CONCLUSION

The covalent attachment of SNAP to the commonly used broad spectrum antibiotic, ampicillin, was successful and it was proven to be a stable, novel NO donating molecule with high antimicrobial capabilities. Confirmation of this attachment was proven via NMR and the overall conversion was quantified through Ellman's assay and by catalytically removing all available NO on the molecule post nitrosation. A synergistic antimicrobial mechanism between the SNAP moiety on the ampicillin molecule was observed as it showed increased biofilm dispersal and a decrease in viable planktonic bacteria when compared to either molecule on its own. The synthesized SNAPicillin was also able to maintain its ability to inhibit bacteria growth by displaying a similar zone of inhibition against S. aureus when compared to pure ampicillin. By potentially incorporating SNAPicillin into polymeric medical devices such as catheters or as a direct response to already formed biofilms related to these devices, the combination of NO release and ampicillin into a single molecule is a promising therapeutic agent in combatting complicated antibiotic resistant infections.

REFERENCES (1) Donlan, R. M., Biofilms: Microbial Life on Surfaces. *Emerg. Infect. Dis.* 2002, 8 (9), 881.
(2) Bjarnsholt, T.; Jensen, P. Ø.; Fiandaca, M. J.; Pedersen, J.; Hansen, C. R.; Andersen, C. B.; Pressler, T.; Givskov, M.; Høiby, N., Pseudomonas aeruginosa Biofilms in the Respiratory Tract of Cystic Fibrosis Patients. *Pediatr. Pulmonol.* 2009, 44 (6), 547-558.
(3) Ceri, H.; Olson, M.; Stremick, C.; Read, R.; Morck, D.; Buret, A., The Calgary Biofilm Device: New Technology for Rapid Determination of Antibiotic Susceptibilities of Bacterial Biofilms. *J. Clin. Microbiol.* 1999, 37 (6), 1771-1776.
(4) Furchgott, R. F., Role of Endothelium in Responses of Vascular Smooth Muscle. *Circ. Res.* 1983, 53 (5), 557-573.
(5) Radomski, M.; Palmer, R.; Moncada, S., Endogenous Nitric Oxide Inhibits Human Platelet Adhesion to Vascular Endothelium. *The Lancet* 1987, 330 (8567), 1057-1058.
(6) MacMicking, J.; Xie, Q.-w.; Nathan, C., Nitric Oxide and Macrophage Function. *Annu. Rev. Immunol.* 1997, 15 (1), 323-350.

(7) Keefer, L. K.; Saavedra, J. E., Nitrogen-Based Diazeniumdiolates: Versatile Nitric Oxide-Releasing Compounds for Biomedical Research and Potential Clinical Applications. *J. Chem. Educ.* 2002, 79 (12), 1427.

(8) Haitham, A.-S. D.; Ferro, A., S-Nitrosothiols: A Class of Nitric Oxide-Donor Drugs. *Clin. Sci.* 2000, 98 (5), 507-520.

(9) Pant, J.; Goudie, M. J.; Hopkins, S. P.; Brisbois, E. J.; Handa, H., Tunable Nitric Oxide Release from S-Nitroso-N-Acetylpenicillamine Via Catalytic Copper Nanoparticles for Biomedical Applications. *ACS Appl. Mater. Interfaces* 2017, 9 (18), 15254-15264.

(10) Lu, Y.; Slomberg, D. L.; Shah, A.; Schoenfisch, M. H., Nitric Oxide-Releasing Amphiphilic Poly (Amidoamine) (Pamam) Dendrimers as Antibacterial Agents. *Biomacromolecules* 2013, 14 (10), 3589-3598.

(11) Hopkins, S. P.; Pant, J.; Goudie, M. J.; Schmiedt, C.; Handa, H., Achieving Long-Term Biocompatible Silicone Via Covalently Immobilized S-Nitroso-N-Acetylpenicillamine (Snap) That Exhibits 4 Months of Sustained Nitric Oxide Release. *ACS Appl. Mater. Interfaces* 2018, 10 (32), 27316-27325.

(12) Hetrick, E. M.; Schoenfisch, M. H., Antibacterial Nitric Oxide-Releasing Xerogels: Cell Viability and Parallel Plate Flow Cell Adhesion Studies. *Biomaterials* 2007, 28 (11), 1948-1956.

(13) Barraud, N.; J Kelso, M.; A Rice, S.; Kjelleberg, S., Nitric Oxide: A Key Mediator of Biofilm Dispersal with Applications in Infectious Diseases. *Curr. Pharm. Des.* 2015, 21 (1), 31-42.

(14) Schairer, D. O.; Chouake, J. S.; Nosanchuk, J. D.; Friedman, A. J., The Potential of Nitric Oxide Releasing Therapies as Antimicrobial Agents. *Virulence* 2012, 3 (3), 271-279.

(15) Ren, H.; Wu, J.; Colletta, A.; Meyerhoff, M. E.; Xi, C., Efficient Eradication of Mature *Pseudomonas aeruginosa* Biofilm Via Controlled Delivery of Nitric Oxide Combined with Antimicrobial Peptide and Antibiotics. *Front. Microbiol.* 2016, 7, 1260.

(16) Reffuveille, F.; Fairfull-Smith, K. E.; Hancock, R. E., Potentiation of Ciprofloxacin Action against Gram-Negative Bacterial Biofilms by a Nitroxide. *Pathogens and disease* 2015, 73 (5).

(17) Craven, M.; Kasper, S.; Canfield, M.; Diaz-Morales, R.; Hrabie, J.; Cady, N.; Strickland, A., Nitric Oxide-Releasing Polyacrylonitrile Disperses Biofilms Formed by Wound-Relevant Pathogenic *Bacteria. J. Appl. Microbiol.* 2016, 120 (4), 1085-1099.

(18) Duong, H. T.; Jung, K.; Kutty, S. K.; Agustina, S.; Adnan, N. N. M.; Basuki, J. S.; Kumar, N.; Davis, T. P.; Barraud, N.; Boyer, C., Nanoparticle (Star Polymer) Delivery of Nitric Oxide Effectively Negates *Pseudomonas aeruginosa* Biofilm Formation. *Biomacromolecules* 2014, 15 (7), 2583-2589.

(19) Namivandi-Zangeneh, R.; Sadrearhami, Z.; Bagheri, A.; Sauvage-Nguyen, M.; Ho, K. K. K.; Kumar, N.; Wong, E. H.; Boyer, C., Nitric Oxide-Loaded Antimicrobial Polymer for the Synergistic Eradication of Bacterial Biofilm. *ACS Macro Letters* 2018, 7 (5), 592-597.

(20) Barraud, N.; Schleheck, D.; Klebensberger, J.; Webb, J. S.; Hassett, D. J.; Rice, S. A.; Kjelleberg, S., Nitric Oxide Signaling in *Pseudomonas aeruginosa* Biofilms Mediates Phosphodiesterase Activity, Decreased Cyclic Di-Gmp Levels, and Enhanced Dispersal. *J. Bacteriol.* 2009, 191 (23), 7333-7342.

(21) Howlin, R. P.; Cathie, K.; Hall-Stoodley, L.; Cornelius, V.; Duignan, C.; Allan, R. N.; Fernandez, B. O.; Barraud, N.; Bruce, K. D.; Jefferies, J., Low-Dose Nitric Oxide as Targeted Anti-Biofilm Adjunctive Therapy to Treat Chronic *Pseudomonas aeruginosa* Infection in Cystic Fibrosis. *Mol. Ther.* 2017, 25 (9), 2104-2116.

(22) Moynihan, H. A.; Roberts, S. M., Preparation of Some Novel S-Nitroso Compounds as Potential Slow-Release Agents of Nitric Oxide in Vivo. *J. Chem. Soc., Perkin Trans.* 1 1994, (7), 797-805.

(23) Ellman, G. L., Tissue Sulfhydryl Groups. *Arch. Biochem. Biophys.* 1959, 82 (1), 70-77.

(24) Khan, A. A. P.; Mohd, A.; Bano, S.; Siddiqi, K.; Asiri, A. M., Spectrophotometric Methods for the Determination of Ampicillin by Potassium Permanganate and 1-Chloro-2, 4-Dinitrobenzene in Pharmaceutical Preparations. *Arabian Journal of Chemistry* 2015, 8 (2), 255-263.

(25) Worley, B. V.; Slomberg, D. L.; Schoenfisch, M. H., Nitric Oxide-Releasing Quaternary Ammonium-Modified Poly (Amidoamine) Dendrimers as Dual Action Antibacterial Agents. *Bioconjug. Chem.* 2014, 25 (5), 918-927.

(26) Privett, B. J.; Deupree, S. M.; Backlund, C. J.; Rao, K. S.; Johnson, C. B.; Coneski, P. N.; Schoenfisch, M. H., Synergy of Nitric Oxide and Silver Sulfadiazine against Gram-Negative, Gram-Positive, and Antibiotic-Resistant Pathogens. *Mol. Pharm.* 2010, 7 (6), 2289-2296.

(27) Verderosa, A. D.; Mansour, S. C.; de la Fuente-Nunez, C.; Hancock, R. E.; Fairfull-Smith, K. E., Synthesis and Evaluation of Ciprofloxacin-Nitroxide Conjugates as Anti-Biofilm Agents. *Molecules* 2016, 21 (7), 841.

(28) Logghe, C.; Van Ossel, C.; D'Hoore, W.; Ezzedine, H.; Wauters, G.; Haxhe, J.-J., Evaluation of Chlorhexidine and Silver-Sulfadiazine Impregnated Central Venous Catheters for the Prevention of Bloodstream Infection in Leukaemic Patients: A Randomized Controlled Trial. *J. Hosp. Infect.* 1997, 37 (2), 145-156.

(29) León, C.; Ruiz-Santana, S.; Rello, J.; Maria, V.; Vallês, J.; Álvarez-Lerma, F.; Sierra, R.; Saavedra, P.; Álvarez-Salgado, F.; Group, C. S., Benefits of Minocycline and Rifampin-Impregnated Central Venous Catheters. *Intensive Care Med.* 2004, 30 (10), 1891-1899.

(30) Osma, S.; Kahveci, Ş.; Kaya, F.; Akalin, H.; Özakin, C.; Yilmaz, E.; Kutlay, O., Efficacy of Antiseptic-Impregnated Catheters on Catheter Colonization and Catheter-Related Bloodstream Infections in Patients in an Intensive Care Unit. *J. Hosp. Infect.* 2006, 62 (2), 156-162.

(31) Meyer, B.; Genoni, A.; Boudier, A.; Leroy, P.; Ruiz-Lopez, M. F., Structure and Stability Studies of Pharmacologically Relevant S-Nitrosothiols: A Theoretical Approach. *The Journal of Physical Chemistry A* 2016, 120 (24), 4191-4200.

(32) Pant, J.; Gao, J.; Goudie, M. J.; Hopkins, S.; Locklin, J.; Handa, H., A Multi-Defense Strategy: Enhancing Bactericidal Activity of a Medical Grade Polymer with a Nitric Oxide Donor and Surface-Immobilized Quaternary Ammonium Compound. *Acta Biomater.* 2017.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A modified antibiotic compound comprising a nitric oxide release agent covalently attached to an antibiotic molecule, wherein the antibiotic molecule is ampicillin, vancomycin, gentamicin, or cephalexin.

2. The modified antibiotic compound of claim 1, wherein the nitric oxide release agent is a S-nitrosothiol selected from the group consisting of: S-nitroso-N-acetylpenicillamine, S-nitroso-glutathione, S-nitroso-N-acetylcysteine, S-nitrosocysteine, S-nitrosopenicillamine, S-nitroso-B,D-glucose, S-nitrosocaptopril, S-nitrosocysteamine, and S-nitroso-3-mercapto-propanoic acid.

3. The modified antibiotic compound of claim 1, wherein the antibiotic molecule is ampicillin.

4. The modified antibiotic compound of claim 1, wherein when an antimicrobially effective amount of the modified antibiotic compound is applied to a biofilm, the modified antibiotic compound is effective to reduce viability of biofilm bacteria by about 99.8% or more.

5. The modified antibiotic compound of claim 1, wherein when an antimicrobially effective amount of the modified antibiotic compound is applied to a biofilm, the modified antibiotic compound is effective to reduce viability of biofilm bacteria dispersed from the biofilm in a planktonic state by about 99.3% or more.

6. A method of making a modified antibiotic compound, comprising:

covalently attaching a nitric oxide release agent to an antibiotic molecule, wherein the attachment is formed by mixing the nitric oxide release agent and the antibiotic molecule in a solvent to form a mixture, and nitrosating the mixture.

7. The method of claim 6, wherein the nitric oxide release agent is N-acetyl penicillamine thiolactone, such that when the mixture is nitrosated a modified antibiotic comprising S-nitroso-N-acetylpenicillamine covalently attached to the antibiotic molecule is formed.

8. The method of claim 6, wherein the antibiotic molecule is ampicillin, vancomycin, gentamicin, or cephalexin.

9. The method of claim 6, wherein nitrosating the mixture comprises addition of t-butyl nitrite to the mixture.

10. The method of claim 6, wherein the nitric oxide release agent and the antibiotic molecule are mixed in about an equimolar ratio.

11. A product with antimicrobial properties, comprising a polymer material and a modified antibiotic compound, where the modified antibiotic compound comprises a nitric oxide release agent covalently attached to an antibiotic molecule.

12. The product of claim 11, wherein the polymer material is CarboSil.

13. The product of claim 11, wherein the modified antibiotic compound comprises S-nitroso-N-acetylpenicillamine covalently attached to ampicillin.

14. The product of claim 11, wherein the modified antibiotic compound is blended with the polymer material to form a polymer film.

15. The product of claim 11, wherein the polymer material is impregnated with the modified antibiotic compound.

16. The product of claim 11, wherein the product forms all or part of a biomedical device.

17. The product of claim 11, wherein the product is selected from the group consisting of a catheter, an IV delivery tube, a stent, a catheter, a PICC line, a feeding tube, a wound dressing, an extracorporeal circuit, a membrane oxygenator, a vascular graft, and an endotracheal tube.

18. The product of claim 17, wherein the modified antibiotic compound is incorporated into the polymer material.

19. The product of claim 17, wherein the polymer material is a thin film applied to the product.

20. The modified antibiotic compound of claim 1, wherein the compound comprises S-nitroso-N-acetylpenicillamine covalently attached to ampicillin.

* * * * *

UNITED STATES PATENT AND TRADEMARK OFFICE
CERTIFICATE OF CORRECTION

| | |
|---|---|
| PATENT NO. | : 11,220,516 B2 |
| APPLICATION NO. | : 17/005373 |
| DATED | : January 11, 2022 |
| INVENTOR(S) | : Hitesh Handa et al. |

It is certified that error appears in the above-identified patent and that said Letters Patent is hereby corrected as shown below:

In the Specification

Prior to the heading CROSS-REFERENCE TO RELATED APPLICATIONS at Column 1, please insert the following:
--STATEMENT REGARDING FEDERALLY SPONSORED RESEARCH OR SUPPORT
This invention was made with government support under grant number R01 HL134899 awarded by the NIH. The government has certain rights in the invention. (37 CFR 401.14 f (4))--

Signed and Sealed this
Twenty-eighth Day of March, 2023

*Katherine Kelly Vidal*

Katherine Kelly Vidal
*Director of the United States Patent and Trademark Office*